United States Patent
Lee et al.

(10) Patent No.: US 8,723,938 B2
(45) Date of Patent: May 13, 2014

(54) IMMUNOASSAY APPARATUS AND METHOD OF DETERMINING BRIGHTNESS VALUE OF TARGET AREA ON OPTICAL IMAGE USING THE SAME

(75) Inventors: Ki-iu Lee, Suwon-si (KR); Chung-ung Kim, Yongin-si (KR); Jong-lin Park, Yonging-si (KR); Dong-hwi Cho, Suwon-si (KR); Su-bong Bae, Suwon-si (KR); Jong-cheol Kim, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 595 days.

(21) Appl. No.: 12/662,132

(22) Filed: Mar. 31, 2010

(65) Prior Publication Data

US 2010/0253770 A1    Oct. 7, 2010

(30) Foreign Application Priority Data

Apr. 2, 2009 (KR) ................. 10-2009-0028534

(51) Int. Cl.
*A61B 1/06* (2006.01)

(52) U.S. Cl.
USPC ............. 348/68; 348/69; 348/131; 348/132; 348/391.1; 382/130

(58) Field of Classification Search
USPC ........... 348/68, 69, 131, 132, 391.1; 382/130
See application file for complete search history.

(56) References Cited

U.S. PATENT DOCUMENTS

| | | | |
|---|---|---|---|
| 8,144,214 B2* | 3/2012 | Yamashita et al. | 348/229.1 |
| 8,189,949 B2* | 5/2012 | Akatsuka | 382/274 |
| 8,301,002 B2* | 10/2012 | Shani | 385/129 |
| 2004/0095360 A1 | 5/2004 | Tseng et al. | |
| 2008/0043117 A1 | 2/2008 | Kim et al. | |
| 2008/0089603 A1* | 4/2008 | Lewis et al. | 382/274 |
| 2008/0287316 A1 | 11/2008 | Spivey et al. | |

FOREIGN PATENT DOCUMENTS

| | | |
|---|---|---|
| JP | 2006-237580 | 9/2006 |
| KR | 10-2004-0065011 | 7/2004 |
| KR | 10-2005-0099297 | 10/2005 |

OTHER PUBLICATIONS

Alexander A. Sawchuck, "Real-Time Correction of Intensity Nonlinearities in Imaging Systems", IEEE Transactions on Computers, vol. C-26, No. 1, Jan. 1977, pp. 34-39.
Extended European Search Report issued Aug. 20, 2012 in corresponding European Patent Application No. 10158097.5.
Maria Lönnberg et al., "Quantitative Detection in the Attomole Range for Immunochromatographic Tests by Means of a Flatbed Scanner", Anayltic Biochemistry 293, Jun. 15, 2001, pp. 224-231.
Radu Ciprian Bilcu et al., "Image Pre-Processing for Bar Code Detection in Mobile Devices", ICASSP, Jan. 1, 2006, pp. 1180-1183.

(Continued)

*Primary Examiner* — Phuoc Nguyen
*Assistant Examiner* — Clarence John
(74) *Attorney, Agent, or Firm* — Staas & Halsey LLP

(57) ABSTRACT

Provided are a method of determining a brightness value of a target area on an optical image, and a computer-readable recording medium including a program for executing the method on a computer. Target brightness values of a plurality of target areas in an optical image are accurately compared with each other by plotting a graph with brightness values depending on positions within a subject.

11 Claims, 9 Drawing Sheets

(56) References Cited

OTHER PUBLICATIONS

Alexander A. Sawchuck, "Real-Time Correction of Intensity Nonlinearities in Imaging Systems", IEEE Transactions on Computers, vol. C-26, No. 1, Jan. 1, 1977, pp. 34-39.

Prasun Mahanti et al., "Improved Signal Extraction from Fluoresence Immunoassay Image Sequences", Asilomar, Oct. 26, 2008, pp. 1975-1978.

Jog Raj et al., "Surface immobilization of antibody on cyclic olefin copolymer for sandwich immunoassay", Biosensors and Bioelectronics 24, Jan. 31, 2009, pp. 2654-2658.

* cited by examiner

IMMUNOASSAY APPARATUS AND METHOD OF DETERMINING BRIGHTNESS VALUE OF TARGET AREA ON OPTICAL IMAGE USING THE SAME

CROSS-REFERENCE TO RELATED APPLICATIONS

This application claims the benefit of Korean Patent Application No. 10-2009-0028534, filed on Apr. 2, 2009, in the Korean Intellectual Property Office, the disclosure of which is incorporated herein in its entirety by reference.

BACKGROUND

Field

An embodiment or embodiments relates to an immunoassay apparatus, a method of determining a brightness value of a target area on an optical image using the immunoassay apparatus, and a non-transitory computer-readable recording medium including a program for executing the method on a computer.

When the levels of brightness of target areas in a single optical image are numerically represented and compared with each other, brightness values of the target areas relative to surrounding areas may be expressed as the sizes of trough curves on a graph. The sizes of the trough curves should be numerically represented to obtain the brightness values of the target areas. To this end, the distance from the base of a trough curve to the lowest value of the trough curve is calculated in the related art. In this case, when a total brightness value to be determined is in a range, it is difficult to numerically represent the gradual variation in the total brightness value. Furthermore, when the trough curve is triangular and not rectangular, it is difficult to numerically represent the entire brightness of the trough curve corresponding to the target area.

SUMMARY

Additional aspects and/or advantages will be set forth in part in the description which follows and, in part, will be apparent from the description, or may be learned by practice of the invention.

An embodiment provides a method of determining a brightness value of a target area on an optical image.

An embodiment also provides a non-transitory computer-readable recording medium including a program for executing the method on a computer.

An embodiment also provides an immunoassay apparatus.

According to another embodiment, there is provided a method of determining a target brightness value of a target area for an immunoassay apparatus, the method including: photographing, with a camera, a subject including a surrounding area and the target area to provide an image of the subject to an image sensor of the camera; converting the image to an electrical signal at the image sensor; determining a second-order approximate equation $y=ax2$ with x denoting a position value within the subject, y denoting a brightness value depending on x, and 'a' denoting a coefficient; determining a difference between y and zero; adding or subtracting the difference to or from y to correct y that is caused by uneven illumination and lens curvature; and determining the target brightness value of the target area according to x and a corrected brightness value y' given by correcting y.

According to another embodiment, there is provided a non-transitory computer-readable recording medium including a program for executing the method of determining a target brightness value of a target area on a computer.

According to another embodiment, there is provided an immunoassay apparatus: an illuminating unit to provide light to a subject including a surrounding area and a target area; a measuring unit to receive the light from the illuminating unit to photograph the subject and to provide an image of the subject, the image including an optical signal; a camera including an image sensor that receives the image and converts the image to an electrical signal; a calculating unit to correct distortion of the image according to the electrical signal and to determine a target brightness value of the target area; and an output unit to output a calculation result including the corrected distortion and the target brightness value.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION OF EMBODIMENTS

Figure 1:
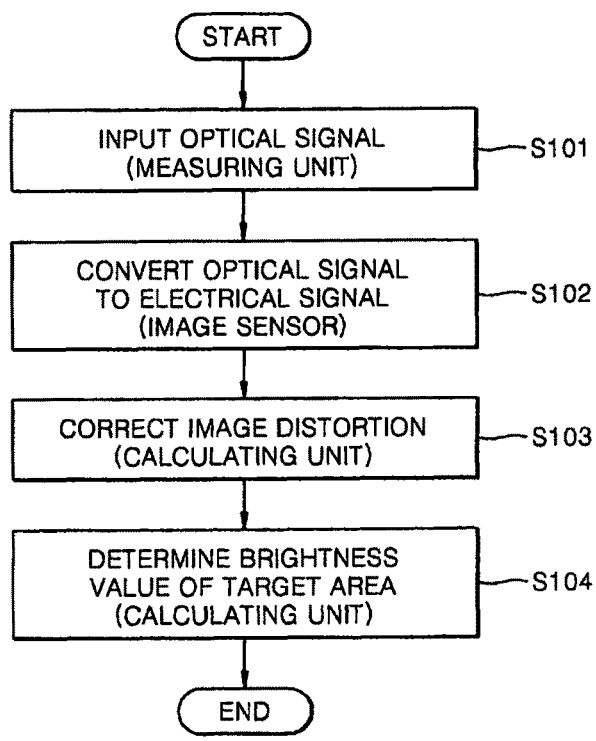
FIG. 1 is a flowchart illustrating a method of determining a brightness value of a target area, according to an embodiment.

Reference will now be made in detail to the embodiments, examples of which are illustrated in the accompanying drawings, wherein like reference numerals refer to the like elements throughout. The embodiments are described below to explain the present invention by referring to the figures.

An embodiment or embodiments will now be described more fully with reference to the accompanying drawings, in which exemplary embodiments of the inventive concept are shown. The inventive concept may, however, be embodied in many different forms and should not be construed as being limited to the embodiments set forth herein; rather, these embodiments are provided so that this disclosure will be thorough and complete, and will fully convey the concept of the inventive concept to those of ordinary skill in the art.

According to an embodiment, there is provided a method of determining a target brightness value of a target area for an immunoassay apparatus, the method including: photographing a subject including a surrounding area and the target area with a camera to provide an image of the subject to an image sensor of the camera; converting the image to an electrical signal at the image sensor; determining a second-order approximate equation $y=ax^2$ with x denoting a position value within the subject, y denoting a brightness value depending on x, and 'a' denoting a correction coefficient; determining a difference between brightness y and brightness of origin point; adding or subtracting the difference to or from y to correct y that is caused by uneven illumination and lens curvature; and determining the target brightness value of the target area according to x and a corrected brightness value y' given by correcting y.

FIG. 1 is a flowchart illustrating a method of determining a target brightness value of a target area, according to an embodiment.

In operation S101, an optical signal from a subject is input to a camera through a lens. In operation S102, an image sensor in the camera receives the optical signal and converts the optical signal to an electrical signal. In operation S103, an origin point (0, 0) is determined at a calculation unit, and a new coordinate system with the origin point (0, 0) is created to determine $y=ax^2$. Then, position values within the subject are assigned to x, and brightness values depending on the position values are assigned to y, so as to determine a coefficient 'a'. Alternatively, a plurality of numbers are sequentially assigned to the coefficient 'a' in order to determine the coefficient 'a'. Then, a corrected brightness value y' is determined by correcting the brightness values using $y=ax^2$ with the determined coefficient 'a', so as to correct image distortion due to the lens. In operation S104, the target brightness value of the target area is determined according to x and y'.

In another embodiment, the method may further include outputting of the target brightness value of the target area.

Hereinafter, the method of determining a target brightness value of a target area will now be described in more detail.

First, a subject including a surrounding area and the target area is photographed with a camera, and an image of the subject is provided to an image sensor of the camera.

The term "subject", which is an object generating an optical signal and providing the optical signal to a camera, may include a surrounding area and a target area and provide an optical image having a high brightness difference between the surrounding area and the target area. For example, since a reaction sheet used in an immune reaction kit has a high brightness difference between a surrounding area, a reaction start portion, and a reaction end portion according to whether an immune reaction occurs, the reaction sheet is used as the subject as described above.

The camera for photographing the subject may be any digital camera including an image sensor.

The term "image sensor" is defined as a device that captures an image using the characteristic of a semiconductor responding to light. Such an image sensor detects, using pixels, various brightness levels and wavelengths of light emitted from a subject, and converts them to electrical values. That is, an image sensor is a semiconductor device converting an optical image to an electrical signal. Such image sensors are classified into a charge-coupled device (CCD) and a complementary metal oxide semiconductor (CMOS). The CCD includes metal oxide semiconductor (MOS) capacitors very close to each other for storing and transferring electric charges. The CMOS employs CMOS technology in which a control circuit and a signal-processing circuit are used as peripheral circuits, and a switching method in which outputs of pixels are sequentially detected by MOS transistors, the number of which is the same as the number of pixels.

Then, the image of the subject is converted into an electrical signal by the image sensor.

Then, $y=ax^2$ is determined based on the electrical signal.

A reference point (origin point) may be determined within an optical image including the subject, and the reference point may be set to zero, so as to determine x based on a distance from the reference point. The left end of the optical image may be set as the reference point zero on an x-axis. For example, when a subject is a reaction sheet used in an immune reaction kit, the left end of the reaction sheet is set as a reference point zero on an x-axis, and a horizontal length of the reaction sheet may be expressed as a distance from the reference point along the x-axis. The range of the x-axis may be expressed in a length unit (e.g. mm or cm) of the subject, but is not limited thereto.

y, which is obtained by converting the brightness of the subject into the electrical signal, may range from 0 to 255, for example. However, it is not limited thereto.

In another embodiment, the determining of the second-order approximate equation $y=ax^2$ may include: setting, as an origin point (0, 0) of $y=ax^2$, a point where the brightness value of the surrounding area is maximum or minimum; and sequentially assigning a plurality of numbers to the coefficient 'a' of $y=ax^2$ so as to select, as the coefficient 'a', the number when the number of both position values and brightness values that are disposed within the surrounding area and satisfy $y=ax^2$ is largest.

In another embodiment, the determining of the second-order approximate equation $y=ax^2$ may include: setting, as an origin point (0, 0) of $y=ax^2$, a point where the brightness value of the surrounding area is maximum or minimum; and selecting, as the coefficient 'a', a mean of values of the coefficient 'a' given by inputting at least 2 position values of the surrounding area and brightness values depending on the at least 2 position values to $y=ax^2$.

In particular, when the surrounding area is of a white-based color, the position value corresponding to the maximum brightness value and the maximum brightness value are set as the coordinates of the origin point (0, 0). On the other hand, when the surrounding area is of a black-based color, the position value corresponding to the minimum brightness value and the minimum brightness value are set as the coordinates of the origin point (0, 0). According to a new coordinate system having the origin (0, 0), the coefficient 'a' is determined. In a method of determining the coefficient 'a', numbers are sequentially assigned to the coefficient 'a' of $y=ax^2$ so as to select, as the coefficient 'a', the number when the number of both position values and brightness values that are disposed within the surrounding area and satisfy $y=ax^2$ is largest. In another method of determining the coefficient 'a', a mean of values of the coefficient 'a' given by inputting at least 2 position values of the surrounding area and brightness values depending on the at least 2 position values to $y=ax^2$ is selected as the coefficient 'a'. In this case, the number of both the at least 2 position values of the surrounding area and the brightness values depending on the at least 2 position values may be increased to obtain an accurate value of the coefficient 'a'.

The methods of determining the coefficient 'a' may be automatically executed by a program, or a tester may manually designate values into $y=ax^2$ on the basis of an output graph.

Lens curvature and uneven illumination on the subject cause distortion in which brightness values depending on position values within the subject decrease or increase from the center of the subject to its edge. This distortion is corrected using $y=ax^2$.

Then, a difference between brightness y and brightness of zero point is determined, and the difference of the brightness is added to or subtracted from y to correct y that is caused by uneven illumination and/or lens curvature.

$y=ax^2$ is a correction equation that is used to correct y, thus correcting image distortion. Hereinafter, a method of correcting image distortion using the correction equation will now be described.

First, a difference between y and brightness of zero point is determined. The difference is zero at the origin point (0, 0), and uneven illumination and/or lens curvature cause the difference to increase toward the edge of the subject. y is corrected by adding the difference to y when the coefficient 'a' is less than zero, and by subtracting the difference from y when the coefficient 'a' is greater than zero. However, the correcting y is not limited thereto.

Thus, the target brightness value of the target area of the optical image can be accurately calculated using the corrected brightness value y' given by correcting y.

Finally, the target brightness value of the target area is determined according to x and y'.

A trough curve of the target area according to x and y' is a straight line or a curved line. When the trough curve is a straight line, a trough curve area defined by the trough curve is triangular or rectangular to easily calculate the trough curve area corresponding to the target brightness value of the target area. When the trough curve is a curved line and a function of the trough curve is known, a trough curve area defined by the trough curve is determined by the integral of the trough curve. However, since the trough curve includes a group of points in an irregular form, it is difficult to accurately determine a trough curve area defined by the trough curve. Thus, the area of a triangle or rectangle that is approximately equal to the trough curve area is determined to calculate the target brightness value of the target area.

In another embodiment, the determining of the target brightness value may include: selecting, as a reference value, a mean of brightness values of y' within the surrounding area; expressing, as $m_1$, a maximum of differences between brightness y' within the target area and brightness of the reference value; expressing, as $n_1$, a difference between position values $x_1$ and $x_2$ within the subject when y' within the target area is equal to the reference value; and calculating $m_1 n_1/2$ as the target brightness value of the target area.

On a graph according to the embodiment, the target brightness value may be the area of a triangle with $n_1$ as its base and $m_1$ as its height.

In another embodiment, the determining of the target brightness value may include: selecting, as a reference value, a mean of brightness values of y' within the surrounding area; expressing, as $m_2$, a difference between y' within the target area and the reference value; expressing, as $n_2$, a difference between brightnesses of position values $x_3$ and $x_4$ within the subject when a value given by adding or subtracting $m_2$ to or from y' within the target area is equal to the reference value; and calculating a maximum of values of $m_2 n_2$ as the target brightness value of the target area.

On a graph according to the embodiment, the target brightness value may be the area of a rectangle with $n_2$ as its base and $m_2$ as its height. The area of the rectangle varies according to y', and the maximum of the areas of rectangles is the target brightness value.

In another embodiment, the determining of the target brightness value may include: selecting, as a reference value, a mean of values of brightness y' within the surrounding area; expressing, as $m_1$, a maximum of differences between brightnesses y' within the target area and the reference value; expressing, as $n_1$, a brightness difference between position values $x_1$ and $x_2$ within the subject when brightness y' within the target area is equal to the reference value; and calculating $m_1 n_1/2$; expressing, as $m_2$, a difference between brightness y' within the target area and the reference value; expressing, as $n_2$, a difference between brightnesses between position values $x_3$ and $x_4$ within the subject when a value given by adding or subtracting $m_2$ to or from brightness y' within the target area is equal to the reference value; and calculating a maximum of values of $m_2 n_2$; and selecting a maximum of $m_1 n_1/2$ and $m_2 n_2$, as the target brightness value of the target area.

When it is difficult to determine whether the trough curve is a triangle or a rectangle on a graph according to the present embodiment, the target brightness value may be the maximum of both a triangle area corresponding to $m_1 n_1/2$ and the maximum of rectangle areas corresponding to $m_2 n_2$.

In another embodiment, the target area may be provided in plurality.

According to another embodiment, there is provided a non-transitory computer-readable recording medium including a program for executing, on a computer, the method of determining a target brightness value of a target area.

The method may also be embodied as computer-readable code on a non-transitory computer-readable recording medium. The non-transitory computer-readable recording medium is any data recording device that stores data which is thereafter read by a computer that is any system processing information. Examples of the non-transitory computer-readable recording medium include read-only memory (ROM), random-access memory (RAM), CD-ROMs, magnetic tapes, floppy disks, and optical data storage.

According to another aspect, there is provided an immunoassay apparatus including: an illuminating unit to provide light to a subject including a surrounding area and a target area; a measuring unit to receive the light from the illuminating unit to photograph the subject and to provide an image of the subject, the image; a camera including an image sensor that receives the image and converts the image to an electrical signal; a calculating unit to correct distortion of the image according to the electrical signal and to determine a target brightness value of the target area; and an output unit to output a calculation result including the corrected distortion and the target brightness value.

In another embodiment, the calculating unit may perform a calculating operation including: determining a second-order approximate equation $y=ax^2$ with x denoting a position value within the subject, y denoting a brightness value depending on x, and 'a' denoting a coefficient; determining a difference between a brightness y and a brightness of zero point; correcting y using the difference that is caused by uneven illumination and lens curvature; and determining the target brightness value of the target area according to x and a corrected brightness value y' given by correcting y.

In another embodiment, the calculating unit may perform a calculating operation including: determining a second-order approximate equation $y=ax^2$ with x denoting a position value within the subject, y denoting a brightness value depending on x, and 'a' denoting a coefficient; determining a difference between a brightness y and a brightness of zero point; adding or subtracting the difference to or from y to correct y that is caused by uneven illumination and lens curvature; and determining the target brightness value of the target area according to x and a corrected brightness value y' given by correcting y.

The immunoassay apparatus is any apparatus determining increase and decrease in expression of a target protein due to an antigen-antibody reaction, and any apparatus photographing, with a camera, a sample generating a light-emitting signal or a color signal through an antigen-antibody reaction to determine the amount of the light-emitting signal or color signal. For example, when a target protein is in contact with a reaction sheet to which an antigen or antibody is adhered, the amount of a light emitting signal or color signal varies according to whether the target protein is present on the reaction sheet or whether the amount of the target protein is large or small on the reaction sheet. When the camera of the immunoassay apparatus photographs the reaction sheet as a subject, the immunoassay apparatus analyzes the amount of a light emitting signal or color signal to output a graph or a value to a user.

Figure 9:
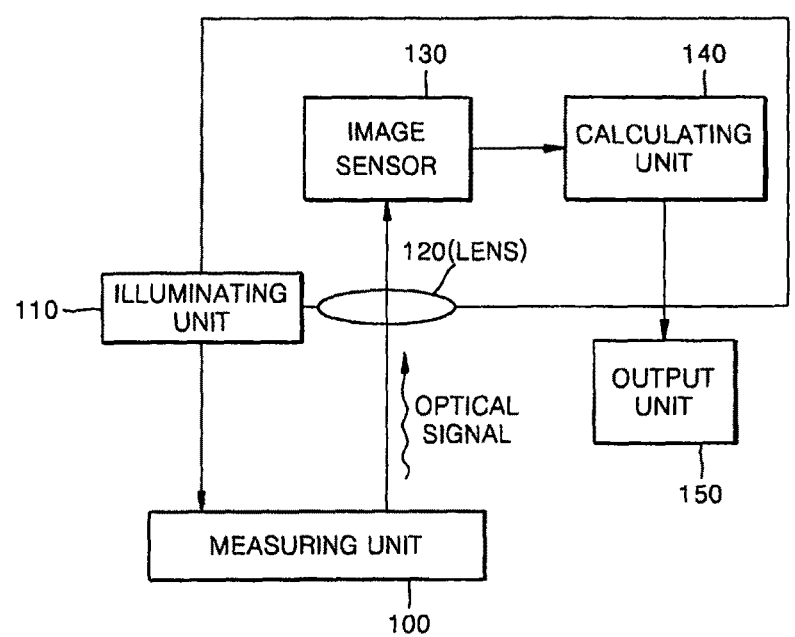
FIG. 9 is a block diagram illustrating an immunoassay apparatus according to an embodiment.

FIG. 9 is a block diagram illustrating an immunoassay apparatus according to an embodiment.

Referring to FIG. 9, an illuminating unit 110 converts a predetermined energy, such as an electrical energy, to light, and provides the light to a subject including a surrounding area and a target area. For example, a light source of the illuminating unit 110 may include any one of an incandescent lamp, a halogen lamp, a fluorescent lamp, a mercury lamp, a metal halide lamp, a xenon lamp, a light emitting diode, and a laser, but is not limited thereto.

A measuring unit 100 receives light from the illuminating unit 110 and forms an image of the subject, and provides the image to an image sensor 130 of a camera through a lens 120.

Since the image sensor 130, a calculating unit 140, and an output unit 150 are the same as those in the description of the method of determining a target brightness value of a target area, their description will be omitted.

EXAMPLE 1

Analyzing Brightness Difference of Image Using Graph

Figure 2:
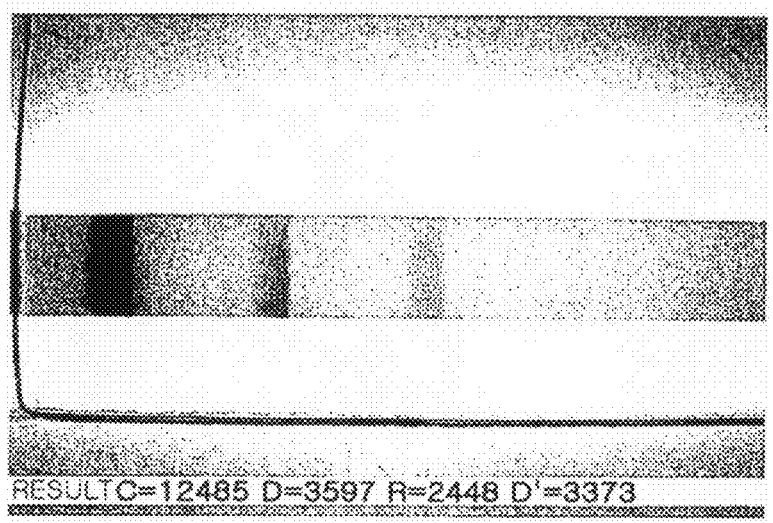
FIG. 2 is an image obtained by photographing a reaction sheet after an immune reaction, according to an embodiment.
Figures 3A, 3B, 3C:
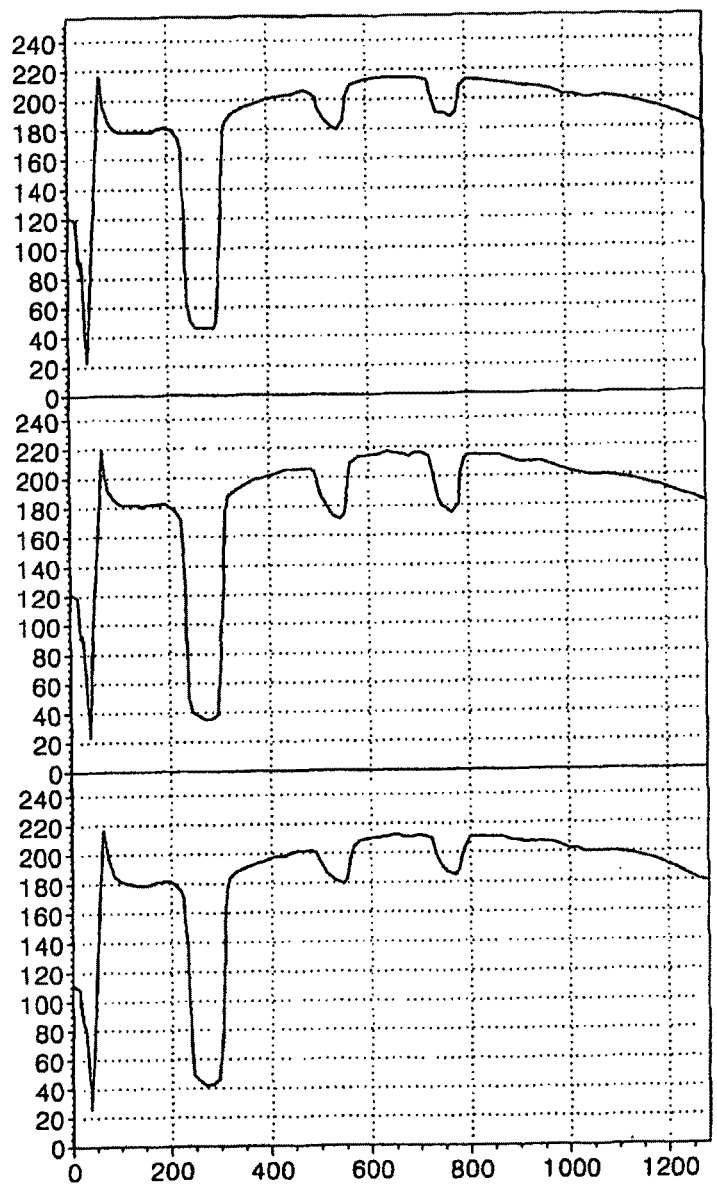
FIGS. 3A-3C are graphs plotted based on the image of FIG. 2.

FIG. 2 is an image obtained by photographing a reaction sheet as a subject under illumination after an immune reaction, according to an embodiment of the inventive concept. FIGS. 3A-3C are graphs with a brightness value, R, G, and B, respectively depending on a position value x within the subject, based on the image of FIG. 2.

Figure 4:
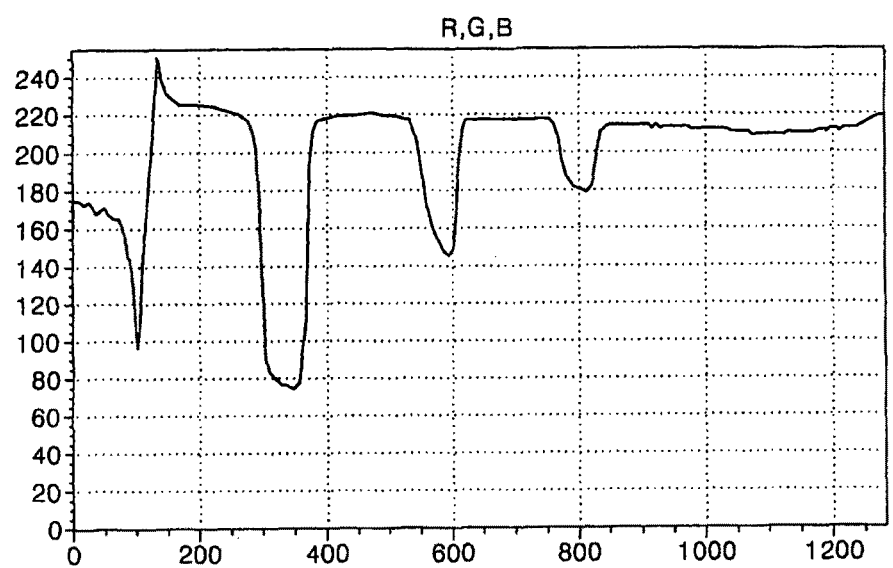
FIG. 4 is a graph obtained by correcting the graphs of FIGS. 3A-3C.

Referring to FIGS. 3A-3C, reaction areas of the reaction sheet where the immune reaction occurs are darker than their surroundings, and the brightness of the reaction sheet varies according to the intensity of the immune reaction. Thus, on the graphs showing analyzed electrical signals, portions corresponding to the reaction areas are recessed. Since the rest of the reaction sheet, except for the reaction areas, has constant brightness, the upper portions of curves plotted with brightness values should have constant values. However, when an optical image is incident into a camera through a lens, the optical image is distorted by the lens. Thus, the upper portions of the curves were convex and not horizontal. FIG. 4 is a graph obtained by correcting the convex curves of FIGS. 3A-3C. Since the convex curve is corrected, the dark reaction areas can be analyzed based on recessed amounts of the recessed portions.

In each of the graphs of FIGS. 3A-3C and 4, an x-axis denotes a horizontal distance with the left end of the reaction sheet as zero, and a y-axis denotes the brightness value of the obtained image. Some portion of trough curves, shown in portions of the graphs where the horizontal distance is close to zero, were excluded when analyzing brightness values within surrounding and target areas of the reaction sheet since the trough curves are not the brightness values within the surrounding and target areas.

EXAMPLE 2

Numerical Representation of Brightness Difference of Image

Figure 7:
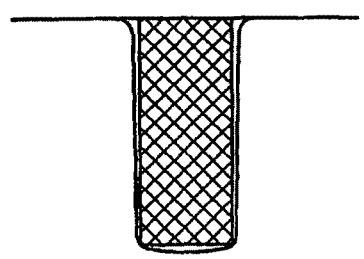
FIG. 7 is a schematic view illustrating a measurable area of an approximately rectangular trough curve plotted with brightness values of target and surrounding areas, according to an embodiment.

FIG. 7 illustrate a measurable area of an approximately rectangular trough curve plotted with brightness values of target and surrounding areas, according to an embodiment.

Figure 8:
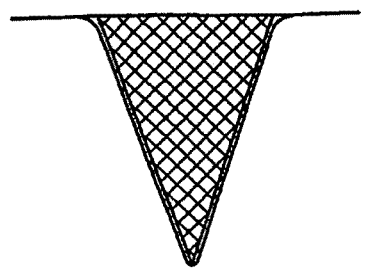
FIG. 8 is a schematic view illustrating a measurable area of an approximately triangular trough curve plotted with brightness values of target and surrounding areas, according to an embodiment.

FIG. 8 illustrate a measurable area of an approximately triangular trough curve plotted with brightness values of target and surrounding areas, according to another embodiment.

Figure 5:
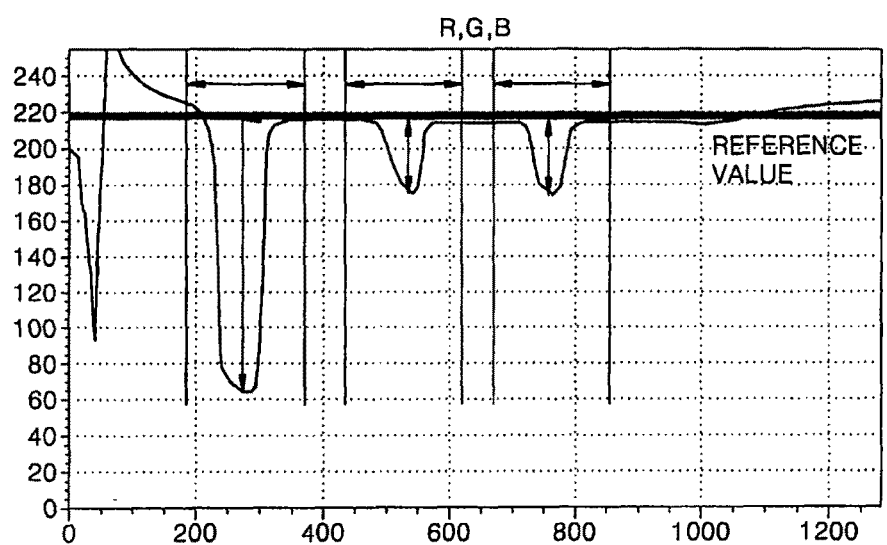
FIG. 5 is a graph illustrating set ranges of a reference value for determining brightness values of target areas, according to an embodiment.

FIG. 5 is a graph illustrating set ranges of a reference value for determining brightness values of target areas, according to as embodiment. Referring to FIG. 5, regions corresponding to the target areas are trough curves, and brightness values of the trough curves are determined based on a triangle area or rectangle area according to shapes of the trough curves. That is, a line, parallel to an x-axis and representing the reference value, includes bases for determining areas that are defined by the trough curves corresponding to the target areas. The lengths of the bases may be made the same to compare the brightness values of the target areas with each other.

Figure 6:
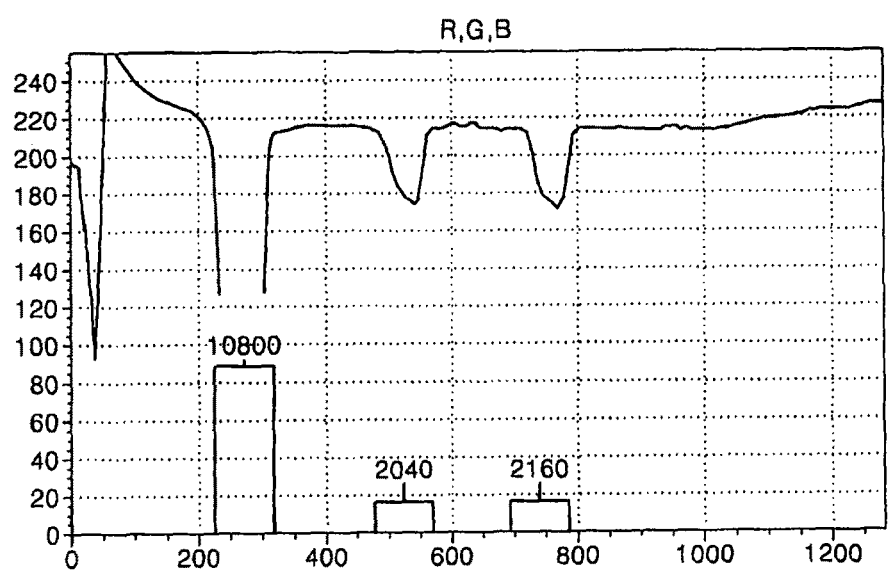
FIG. 6 is brightness values of the target areas according to the set ranges of FIG. 5.

FIG. 6 is a graph obtained by calculating the brightness values of the target areas according to the set ranges of FIG. 5. Therefore, it was found that calculating of approximate values of the areas defined by the trough curves is more accurate than calculating of the lowest values of the trough curves, in expressing brightness differences between the target areas.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A method of determining a target brightness value of a target area for an immunoassay apparatus, the method comprising:

photographing, with a camera, a subject comprising a surrounding area and the target area to provide an image of the subject to an image sensor of the camera;

converting the image to an electrical signal at the image sensor;

determining a second-order approximate equation $y=ax^2$ with x denoting a position value within the subject, y denoting a brightness value depending on x, and 'a' denoting a coefficient such that $y=ax^2$ approximates a light intensity difference that is caused by uneven illumination and/or lens curvature;

determining a difference between y and a brightness value of zero point (origin point);

correcting y using the difference;

determining the target brightness value of the target area according to x and a corrected brightness value y' given by correcting y, setting, as an origin point (0, 0) of $y=ax^2$, according to the maximum or minimum brightness value of the surrounding area.

2. The method of claim 1, wherein the determining of the second-order approximate equation y=ax.sup.2 comprises:

sequentially assigning a plurality of numbers to the coefficient 'a' of y=ax.sup.2 so as to select, as the coefficient 'a', the number when the number of both position values and brightness values that are disposed within the surrounding area and satisfy y=ax.sup.2 is largest.

3. The method of claim 1, wherein the determining of the second-order approximate equation y=ax.sup.2 comprises:

selecting, as the coefficient 'a', a mean of values of the coefficient 'a' given by inputting at least 2 position values of the surrounding area and brightness values depending on the at least 2 position values to y=ax.sup.2.

4. The method of claim 1, wherein the target area is provided in plurality.

5. The method of claim 1, further comprising outputting the target brightness value of the target area.

6. The method of claim 1, the correcting y is adding or subtracting the difference to or from y.

7. A non-transitory computer-readable recording medium comprising a program for executing the method of claim 1 on a computer.

8. A method of determining a target brightness value of a target area for an immunoassay apparatus, the method comprising:
   photographing, with a camera, a subject comprising a surrounding area and the target area to provide an image of the subject to an image sensor of the camera;
   converting the image to an electrical signal at the image sensor;
   determining a second-order approximate equation $y=ax^2$ with x denoting a position value within the subject, y denoting a brightness value depending on x, and 'a' denoting a coefficient such that $y=ax2$ approximates a light intensity difference that is caused by uneven illumination and/or lens curvature;
   determining a difference between y and a brightness value of zero point (origin point);
   correcting y using the difference; and
   determining the target brightness value of the target area according to x and a corrected brightness value y' given by correcting y,
   wherein the determining of the target brightness value comprises:
   selecting, as a reference value, a mean of values of y' within the surrounding area;
   expressing, as $m_1$, a maximum of differences between y' within the target area and the reference value;
   expressing, as $n_1$, a difference between position values $x_1$ and $x_2$ within the subject when y' within the target area is equal to the reference value; and
   calculating $m_1 n_1/2$ as the target brightness value of the target area.

9. A method of determining a target brightness value of a target area for an immunoassay apparatus, the method comprising:
   photographing, with a camera, a subject comprising a surrounding area and the target area to provide an image of the subject to an image sensor of the camera;
   converting the image to an electrical signal at the image sensor;
   determining a second-order approximate equation $y=ax^2$ with x denoting a position value within the subject, y denoting a brightness value depending on x, and 'a' denoting a coefficient such that $y=ax2$ approximates a light intensity difference that is caused by uneven illumination and/or lens curvature;
   determining a difference between y and a brightness value of zero point (origin point);
   correcting y using the difference; and
   determining the target brightness value of the target area according to x and a corrected brightness value y' given by correcting y,
   wherein the determining of the target brightness value comprises:
   selecting, as a reference value, a mean of brightness values of y' within the surrounding area;
   expressing, as $m_2$, a difference brightnesses between y' within the target area and the reference value;
   expressing, as $n_2$, a difference brightnesses between position values $x_3$ and $x_4$ within the subject when a value given by adding or subtracting $m_2$ to or from y' within the target area is equal to the reference value; and
   calculating a maximum of values of $m_2 n_2$ as the target brightness value of the target area.

10. A method of determining a target brightness value of a target area for an immunoassay apparatus, the method comprising:
   photographing, with a camera, a subject comprising a surrounding area and the target area to provide an image of the subject to an image sensor of the camera;
   converting the image to an electrical signal at the image sensor;
   determining a second-order approximate equation $y=ax^2$ with x denoting a position value within the subject, y denoting a brightness value depending on x, and 'a' denoting a coefficient such that $y=ax2$ approximates a light intensity difference that is caused by uneven illumination and/or lens curvature;
   determining a difference between y and a brightness value of zero point (origin point);
   correcting y using the difference; and
   determining the target brightness value of the target area according to x and a corrected brightness value y' given by correcting y,
   wherein the determining of the target brightness value comprises:
   selecting, as a reference value, a mean of values of y' within the surrounding area;
   expressing, as $m_1$, a maximum of differences between y' within the target area and the reference value;
   expressing, as $n_1$, a difference between position values $x_1$ and $x_2$ within the subject when y' within the target area is equal to the reference value; and
   calculating $m_1 n_1/2$;
   expressing, as $m_2$, a difference between y' within the target area and the reference value;
   expressing, as $n_2$, a difference between position values $x_3$ and $x_4$ within the subject when a value given by adding or subtracting $m_2$ to or from y' within the target area is equal to the reference value;
   calculating a maximum of values of $m_2 n_2$; and
   selecting a maximum of $m_1 n_1/2$ and $m_2 n_2$, as the target brightness value of the target area.

11. An immunoassay apparatus comprising:
   an illuminating unit to provide light to a subject comprising a surrounding area and a target area;
   a measuring unit to receive the light from the illuminating unit to photograph the subject and providing an image of the subject, the image comprising an optical signal;
   a camera comprising an image sensor that receives the image and converts the image to an electrical signal;
   a calculating unit to correct distortion of the image according to the electrical signal and to determine a target brightness value of the target area; and
   an output unit to output a calculation result comprising the corrected distortion and the target brightness value,
   wherein the calculating unit performs a calculating operation comprising:
   determining a second-order approximate equation $y=ax^2$ with x denoting a position value within the subject, y denoting a brightness value depending on x, and 'a' denoting a coefficient such that $y=ax^2$ approximates a light intensity difference that is caused by uneven illumination and/or lens curvature;

determining a difference between brightness y and brightness at zero point;

adding or subtracting the difference to or from y to correct y;

determining the target brightness value of the target area according to x and a corrected brightness value y' given by correcting y, and setting, as an origin point (0, 0) of $y=ax^2$, according to the maximum or minimum brightness value of the surrounding area.

* * * * *

UNITED STATES PATENT AND TRADEMARK OFFICE
CERTIFICATE OF CORRECTION

PATENT NO. : 8,723,938 B2
APPLICATION NO. : 12/662132
DATED : May 13, 2014
INVENTOR(S) : Ki-ju Lee et al.

It is certified that error appears in the above-identified patent and that said Letters Patent is hereby corrected as shown below:

On the Title Page

Column 1, Line 3, Item [75] (Inventors), Delete "Yonging-si" and insert -- Yongin-si --, therefor.

Column 2, Line 8, Item [56] (Other Publications), Delete "Anayltic" and insert -- Analytic --, therefor.

On the Page 2, Column 2, Line 1, Item [56] (Other Publications), Delete "Fluoresence" and insert -- Fluorescence --, therefor.

In the Claims

Column 9, Line 26, In Claim 8, Delete "y=ax2" and insert -- $y=ax^2$ --, therefor.

Column 9, Line 57, In Claim 9, Delete "y=ax2" and insert -- $y=ax^2$ --, therefor.

Column 10, Line 22, In Claim 10, Delete "y=ax2" and insert -- $y=ax^2$ --, therefor.

Signed and Sealed this
Thirteenth Day of January, 2015

Michelle K. Lee
*Deputy Director of the United States Patent and Trademark Office*